(12) United States Patent
Yamaguchi et al.

(10) Patent No.: US 6,702,299 B2
(45) Date of Patent: Mar. 9, 2004

(54) CLOSURE STRUCTURE WITH A PLUG (75) Inventors: Shuichi Yamaguchi, Kurume (JP); Hikaru Ibi, Saga-ken (JP); Hirotoshi Tateishi, Tosu (JP)

(73) Assignee: Daiden Co., Ltd. (JP)

( * ) Notice: Subject to any disclaimer, the term of this patent is extended or adjusted under 35 U.S.C. 154(b) by 0 days.

(21) Appl. No.: 10/235,654

(22) Filed: Sep. 6, 2002

(65) Prior Publication Data
US 2003/0047884 A1 Mar. 13, 2003

(30) Foreign Application Priority Data

Sep. 10, 2001 (JP) ..................... P2001-273234

(51) Int. Cl.⁷ .................. F16J 15/02; F16L 55/10; F16L 17/00; B65D 53/00; B65D 51/16
(52) U.S. Cl. ................... 277/628; 277/604; 277/637; 138/90; 285/336; 220/233; 215/313; 222/563
(58) Field of Search ............... 49/475.1, 476.1; 220/DIG. 19, 233, 292; 222/552, 554, 563, 521, 546; 53/432; 215/313, 314, 309; 138/89–90, 96 R, 96 T; 277/314, 316, 602, 604, 628, 630, 637, 644, 650; 285/15, 42, 56, 60, 336, 338, 346

(56) References Cited

U.S. PATENT DOCUMENTS

| | | | | |
|---|---|---|---|---|
| 1,814,678 A | * | 7/1931 | Ferguson | 29/525 |
| 3,893,487 A | * | 7/1975 | Engelking | 138/89 |
| 4,102,472 A | * | 7/1978 | Sloan, Jr. | 220/295 |
| 5,291,619 A | * | 3/1994 | Adorjan | 4/252.6 |
| 6,003,557 A | * | 12/1999 | Brelig et al. | 138/89 |
| 6,070,910 A | * | 6/2000 | Hodges | 285/2 |
| 6,161,841 A | * | 12/2000 | Shaw | 277/642 |
| 6,325,389 B1 | * | 12/2001 | Sharify | 277/604 |
| 6,331,632 B1 | * | 12/2001 | Reedy et al. | 548/148 |

* cited by examiner

*Primary Examiner*—Anthony Knight
*Assistant Examiner*—Vishal Patel
(74) *Attorney, Agent, or Firm*—Rader, Fishman & Grauer PLLC (57) ABSTRACT

A closure includes an object to be closed. The object having an opening hole, a plug member to be inserted into the opening hole, and a seal member disposed on the plug member. The seal member is formed of a ring-shaped elastic member and contacts the object to be closed and the plug member to close the object. An insertion portion of the plug member is smaller than the opening hole. An insertion portion of the plug member is provided with a seal member-receiving groove and is smaller than the opening hole. The seal member-receiving groove is provided with a seal member-seating portion, which has an outer surface with a predetermined diameter smaller than that of the opening hole and larger than that of a bottom of the seal member-receiving groove. The seal member has a cross-sectional shape, which can be fitted into the seal member-receiving groove of the plug member. The seal member has an outer diameter larger than the opening hole in a mounting state into the seal member-receiving groove. The seal member has an elastic deformability by which the seal member, to which an external force is applied, can be deformed so that a thickness thereof in an axial direction reaches at least the predetermined length. The seal member has opposite ends that face in the axial direction, and serve as contact surfaces, which come into contact with the object to be closed and the seal member-seating portion of the plub member.

4 Claims, 8 Drawing Sheets

PRIOR ART

Fig.8

PRIOR ART

CLOSURE STRUCTURE WITH A PLUG

BACKGROUND OF THE INVENTION

1. Field of the Invention

The present invention relates to a closure structure with a plug, in which an opening hole of an object to be closed is closed by means of a plug, and especially to such a closure structure, which has a simple structure and ensures a watertight closing condition.

2. Description of the Related Art

With respect to an indicator, which optically detects and indicates specific gravity of electrolyte, which is received in a battery, utilizing relationship between the specific gravity and refractive index of the electrolyte, there has conventionally been known a plug-type indicator, which is to be mounted on an upper lid of the battery. Of the conventional indicators, there has generally been used the indicator in which a ball that floats or sinks in the electrolyte in accordance with variation of specific gravity and an upper level of the electrolyte is disposed in a lower portion of a plug member, which is formed of a transparent material and is immersed into the electrolyte. In such an indicator, light entering from the upper side of the plug member is made reflect perfectly from a predetermined reflecting surface to enter a position in which the ball is disposed, and light, which is reflected from the ball or pass through it, is made again reflect perfectly from the reflecting surface to return the light to the upper side so as to provide images, which are different in color and indicate variation of the specific gravity and the upper level of the electrolyte.

When the plug member is fitted into an opening hole of an object to be closed, for example, such an indicator is mounted on the upper lid of the battery, there may be a gap between the object to be closed and the plug member, leading to leakage of liquid received in the object to be closed. In order to prevent such a problem, there has conventionally been used a closure structure, which permits to seal the gap between the object to be closed and the plug member to provide a watertight closing condition.

Figure 7:
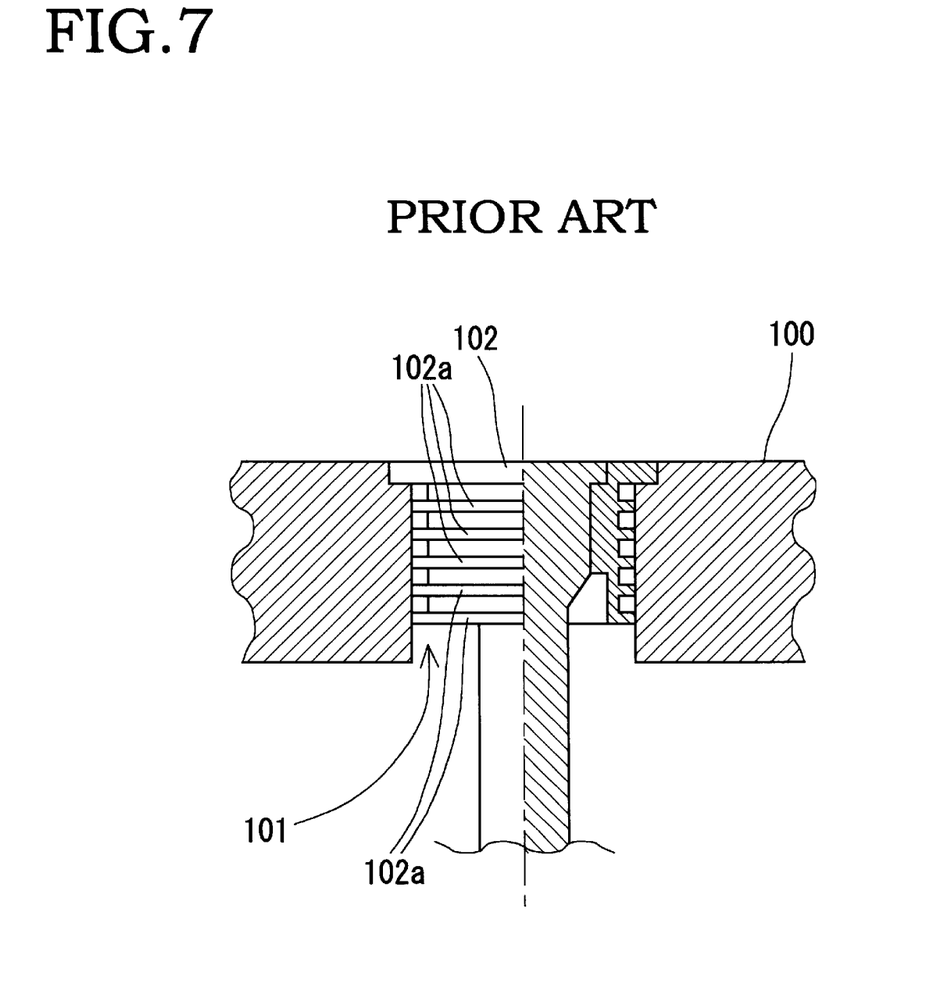
FIG. 7 is a schematic descriptive view of the conventional closure structure.

An example of such a conventional closure structure is shown in FIG. 7. FIG. 7 is a schematic descriptive view of the conventional closure structure.

The conventional structure as shown in FIG. 7 has a structure in which a plug member 102, which has a plurality of flange portions formed on the outer periphery of the plug member 102 so as to extend outward, is fitted into an opening hole 101 of an upper lid 100 of a battery serving as an object to be closed, thus closing the opening hole 101 by means of the plug member 102. The flange portions 102a of the plug member 102 are formed of the same material as the upper lid 100 and have an outside diameter, which is slightly larger than the diameter of the opening hole 101. Forcedly pressing the plug member 102 into the opening hole 101 causes the flange portions 102a to be urged strongly against the upper lid 100, while being deformed, thus making it possible to secure firmly the plug member 102 to the upper lid 100 and prevent leakage of liquid received in the battery.

In the conventional closure structure having the above-described structure, it is difficult to control uniformly deformation of the flange portions 102a in the opening hole 101. As a result, a part of the outer periphery of the flange portion 102a may not come into contact with the upper lid 100, thus causing a gap. Such a gap makes it impossible to maintain the watertight condition, thus causing leakage of liquid as received and leading to occurrence of serious problems.

Figure 8:
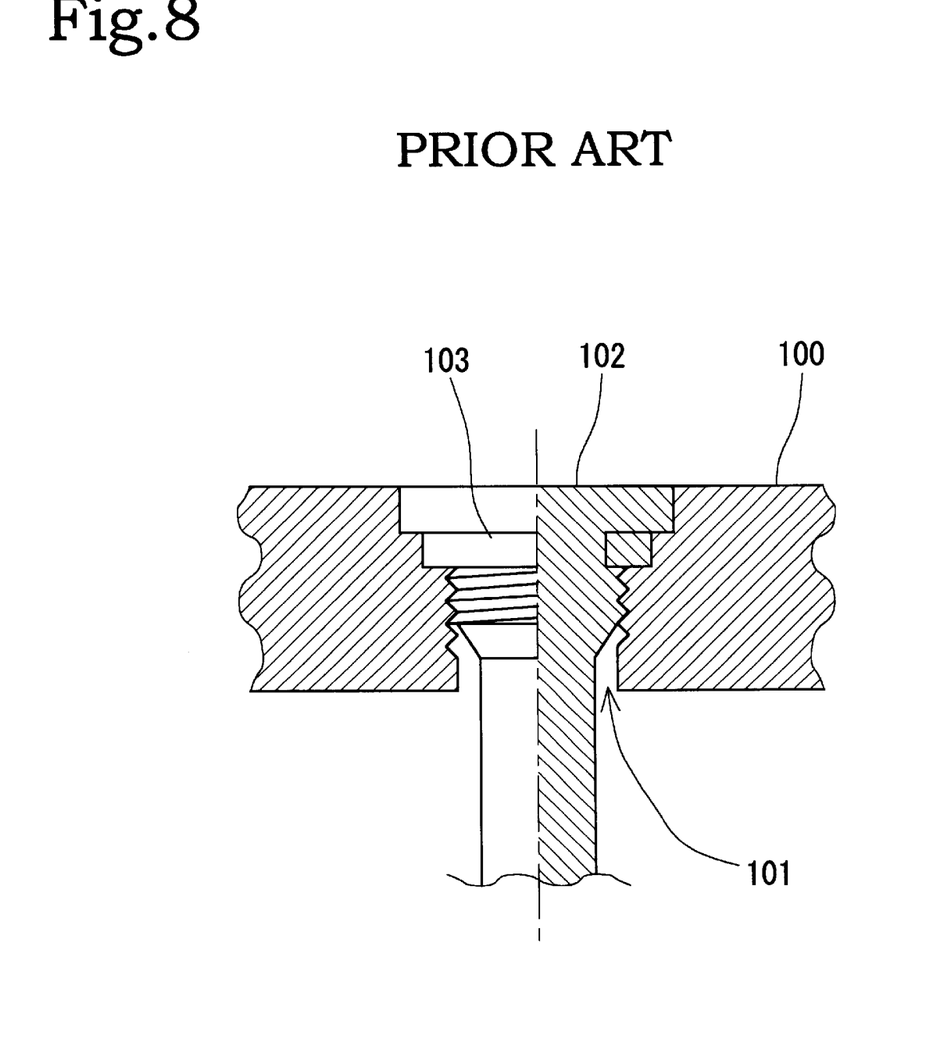
FIG. 8 is a schematic descriptive view of the other conventional closure structure.

Alternatively, there also exists the other conventional closure structure as shown in FIG. 8, in which a plug member 102 on the outer periphery thereof a seal member 103 is mounted, is screwed into an upper lid 100 so as to bring the seal member 103 into contact with the plug member 102 and the upper lid 100, thus closing an opening hole 101.

In this case, the seal member 103 comes surely into contact with the plug member 102 and the upper lid 100, thus providing a sufficient watertight condition. However, formation of screwed portions on the upper lid 100 and the plug member 102 makes the structure complicated. In addition, the screwing operation of the plug member 102 into the upper lid 100 requires much labor in comparison with the case where the plug member 102 is forcedly inserted into the upper lid. Consequently, the cost of the second conventional closure structure is relatively high.

SUMMARY OF THE INVENTION

An object of the present invention, which was made to solve the above-mentioned problems, is therefore to provide a closure structure with a plug member, has a simple structure with a seal member, thus providing a reliable watertight condition, and permits an easy and rapid fitting operation of the plug member.

In order to attain the aforementioned object, a closure structure of the present invention comprises:

an object to be closed with a plug member, said object to be closed having an opening hole formed thereon;

a plug member to be inserted into said opening hole; and a seal member disposed on an outer periphery of said plug member, said seal member being formed of a ring-shaped elastic member, said seal member being to be brought into contact with said object to be closed and said plug member so as to close said object to be closed, wherein:

at least an insertion portion of said plug member, which is to be inserted into said opening hole, is smaller than said opening hole, said insertion portion being provided at an outer periphery of a predetermined portion thereof with a seal member-receiving groove, which extends continuously in a circumferential direction of said insertion portion and has a predetermined depth, and said seal member-receiving groove being provided at a predetermined portion thereof, which is placed on a rear side relative to an insertion direction of said insertion portion, with a seal member-seating portion, which has an outer surface with a predetermined diameter, which is smaller than that of said opening hole by a predetermined length and larger than that of a bottom of said seal member-receiving groove; and said seal member has a cross-sectional shape, which can be fitted into said seal member-receiving groove of said plug member, said seal member having an outer diameter, which is larger than a diameter of said opening hole in a mounting state into said seal member-receiving groove, said seal member having an elastic deformability by which said seal member, to which an external force is applied, can be deformed so that a thickness thereof in an axial direction reaches at least said predetermined length, and said seal member having opposite end faces in the axial direction, which serve as contact surfaces coming into contact with said object to be closed with the plug and said seal member-seating portion of said plug member.

According to the features of the first aspect of the present invention, the plug member is provided on its outer periphery with the seal member-receiving grove portion for mounting the seal member and with the seal member-seating portion having the predetermined outside diameter. Inserting the plug member, to the seal member-receiving groove portion of which the seal member is fitted, into the opening hole causes the outer peripheral portion of the seal member to be elastically deformed from the initial position in the seal member-receiving groove portion toward the opposite direction to the insertion direction of the plug member, under reaction force applied from the object to be closed to the outer peripheral edge of the end face of the seal member in the axial direction thereof, due to insertion force applied to the plug member, while keeping the inner peripheral edge of the end face of the seal member in contact with the seal member-receiving groove portion. The opposite end faces of the seal member in the axial direction thereof, which have been kept in a non-deformed state before insertion of the plug member into the opening hole, come into close contact with the object to be closed and the seal member-seating portion, respectively, after insertion of the plug member into it. Accordingly, when the plug member having the seal member the size of which is so large as to provide a sufficient sealing property is inserted into the opening hole, the seal member is elastically deformed so that the outer peripheral portion of the seal member extends from the initial position in the seal member-receiving groove portion toward the seal member-seating portion, thus preventing the seal member from sliding relative to the object to be closed and decreasing frictional resistance during an inserting operation of the plug member. In addition, the opposite end faces of the seal member come into close contact with the object to be closed and the seal member-seating portion, respectively, thus ensuring a sufficiently large contact area to provide a sealing condition. As a result, it is possible to insert easily the plug member into the opening hole as well as provide a reliable watertight condition.

In the second aspect of the present invention, said plug member may be provided on a rear side of said seal member-seating portion relative to the insertion direction of said plug member with a seal member-restricting portion, which has an outside diameter larger than that of said seal member-seating portion.

According to the feature of the second aspect of the present invention, the plug member is provided with the seal member-restricting portion, which has the outside diameter larger than that of the seal member-seating portion, so that the seal member-restricting portion prevents the seal member from moving relative to the plug member in the opposite direction to the insertion direction of the plug member. It is therefore possible to prevent the seal member from moving excessively relative to the plug member in the opposite direction to the insertion direction of the plug member so as to be apart from the seal member-receiving groove portion, thus holding the seal member in the seal member-seating portion in an appropriate manner. Pulling the plug member from the opening hole causes the seal member to move from the seal member-seating portion to the seal member-receiving groove portion, thus decreasing sliding resistance of the seal member relative to the inner surface of the object to be closed and making it possible to carry out easily a removing operation of the plug member.

In the third aspect of the present invention, said plug member may be provided on a front side of said seal member-seating portion relative to the insertion direction of said plug member with a seal member-urging projection having a flange-shape, said seal member-urging projection having a diameter, which is larger than said seal member-seating portion, said diameter of said seal member-urging projection being predetermined so as not to prevent said seal member from moving from said seal member-receiving groove portion to an outer surface of said seal member-seating portion.

According to the feature of the third aspect of the present invention, the plug member is provided with the flange-shaped seal member-urging projection, which has the diameter larger than the seal member-seating portion. The seal member is more strongly pressed between the seal member-urging projection and the object to be closed in comparison with the other portion, to be elastically deformed, so that the seal member strongly comes close contact with the outer peripheral surface of the seal member-urging projection and the object to be closed, under restoring force in accordance with deformation of the seal member. It is therefore possible to enhance the sealing property over the entire circumference of the seal member, while maintaining the compact structure of the sealed portion without substantially increasing the contact area of the seal member with the plug member and the object to be closed. In addition, it is possible to ensure the reliable watertight condition, even when there occurs variations in size of the opening hole of the object to be closed.

In the fourth aspect of the present invention, said seal member, which is kept in a non-fitting state to said plug member, may have a cross-section so that a thickness on an inner peripheral side of said seal member in the axial direction thereof is larger than a thickness on an outer peripheral side thereof.

According to the feature of the fourth aspect of the present invention, there is used the seal member having the cross-section so that the thickness on the inner peripheral side of the seal member in the axial direction thereof is larger than the thickness on the outer peripheral side thereof. The seal member is more strongly pressed at the front side of thereof in the insertion direction of the plug member, in which the above-mentioned inner peripheral side is placed in the closed state, in comparison with the other portion, to be elastically deformed, so that the seal member strongly comes close contact with the outer peripheral surface of the seal member-seating portion and the object to be closed, under restoring force in accordance with deformation of the seal member. It is therefore possible to enhance the sealing property over the entire circumference of the seal member, while maintaining the compact structure of the sealed portion without substantially increasing the contact area of the seal member with the plug member and the object to be closed. In addition, it is possible to ensure the reliable watertight condition, even when there occurs variations in size of the opening hole of the object to be closed.

DETAILED DESCRIPTION OF THE PREFERRED EMBODIMENTS

[First Embodiment of the Present Invention]

Figure 1:
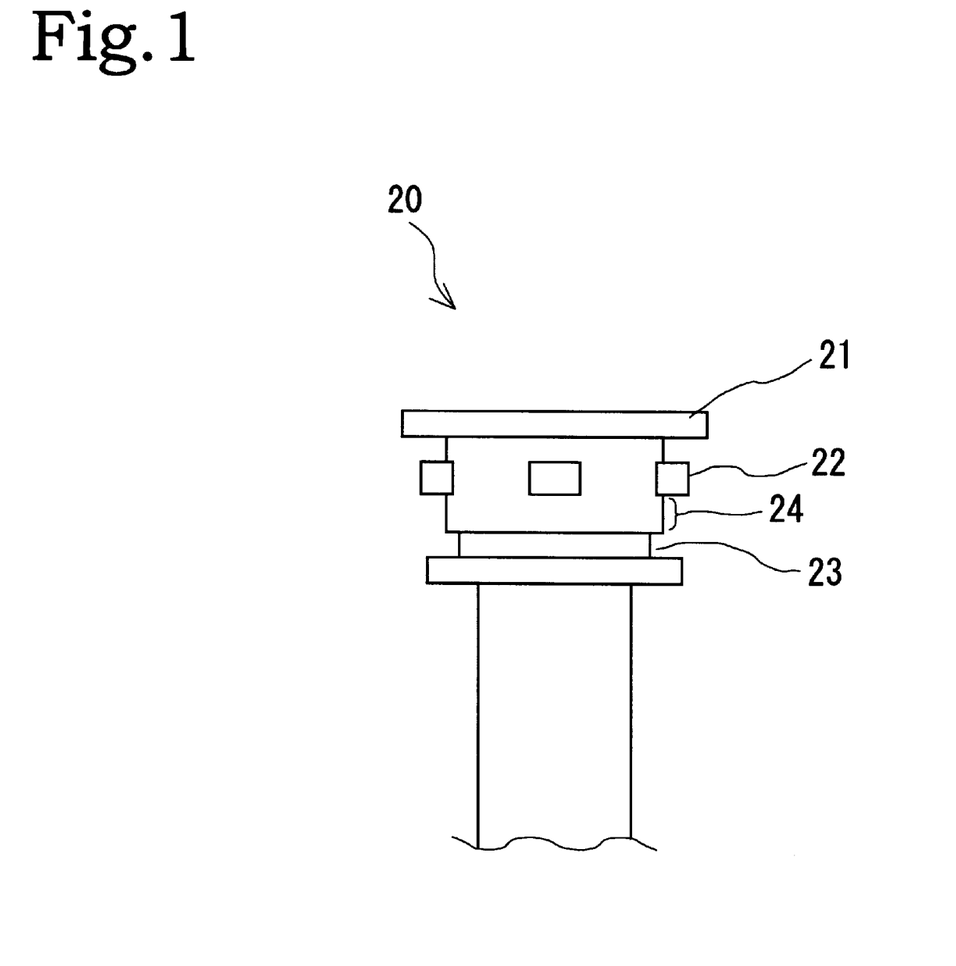
FIG. 1 is a partial front view of a plug member constituting a closure structure of the first embodiment of the present invention.
Figure 2A:
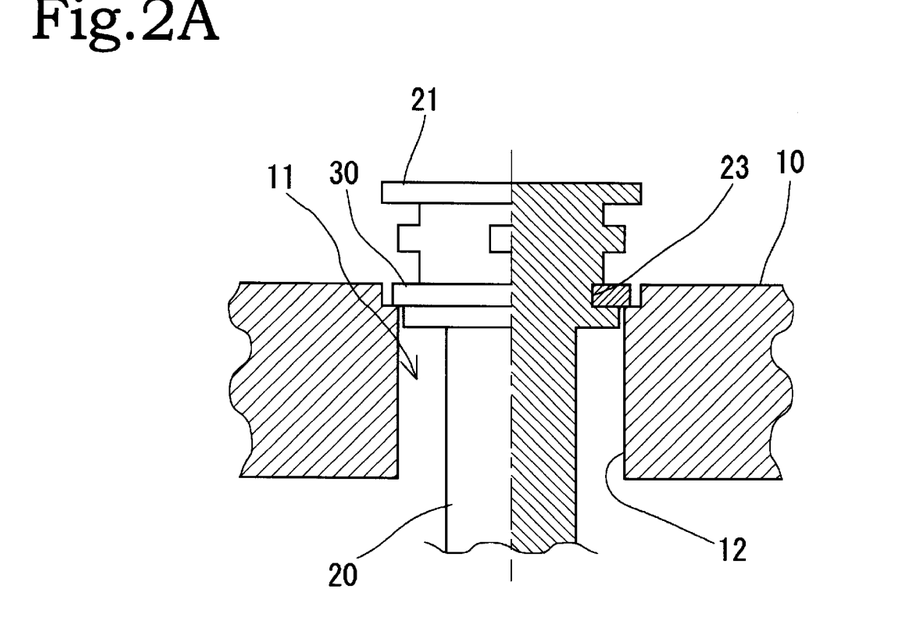
FIGS. 2(A) and 2(B) are descriptive views illustrating a state in which an inserting operation of the plug member of the closure structure of the first embodiment of the present invention is started.
Figure 2B:
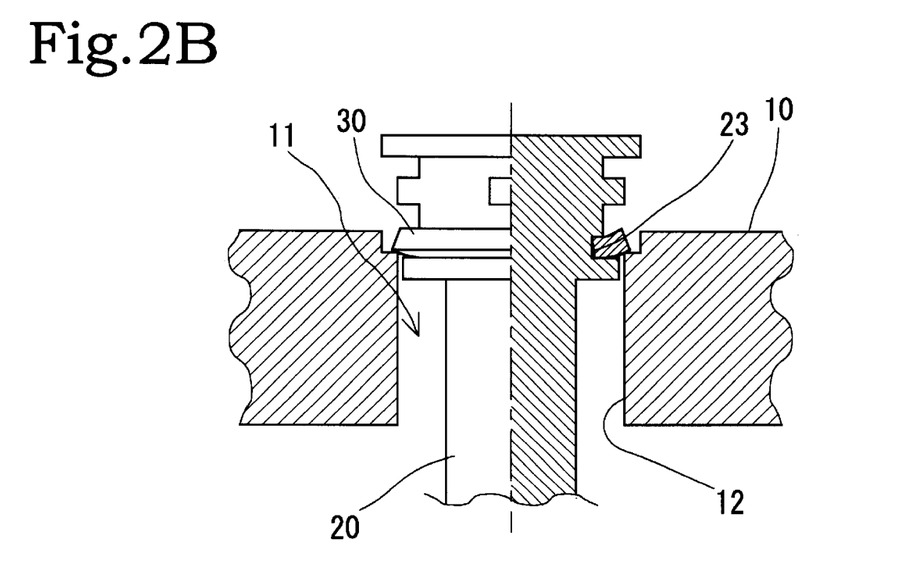
Figure 3A:
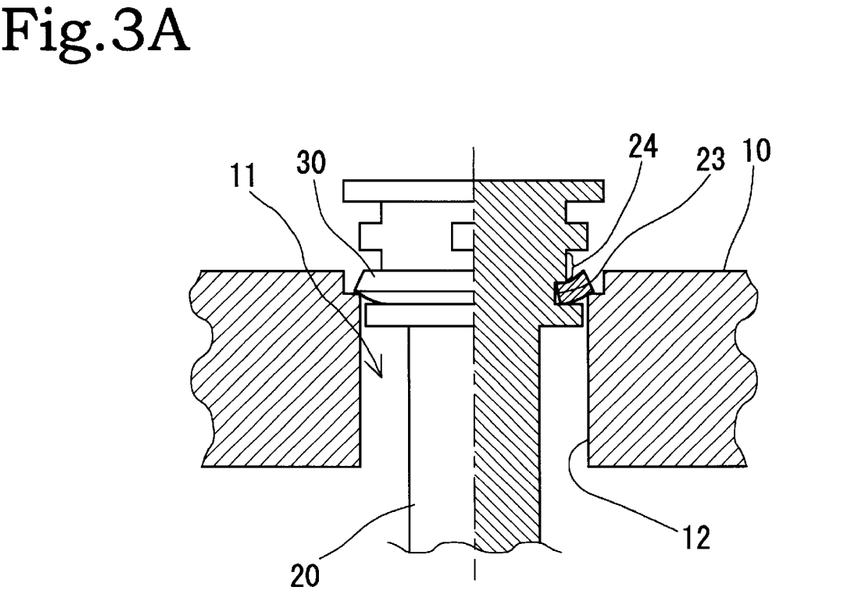
FIGS. 3(A) and 3(B) are descriptive views illustrating a state in which a seal member is elastically deformed during the inserting operation of the plug member of the closure structure of the first embodiment of the present invention.
Figure 3B:
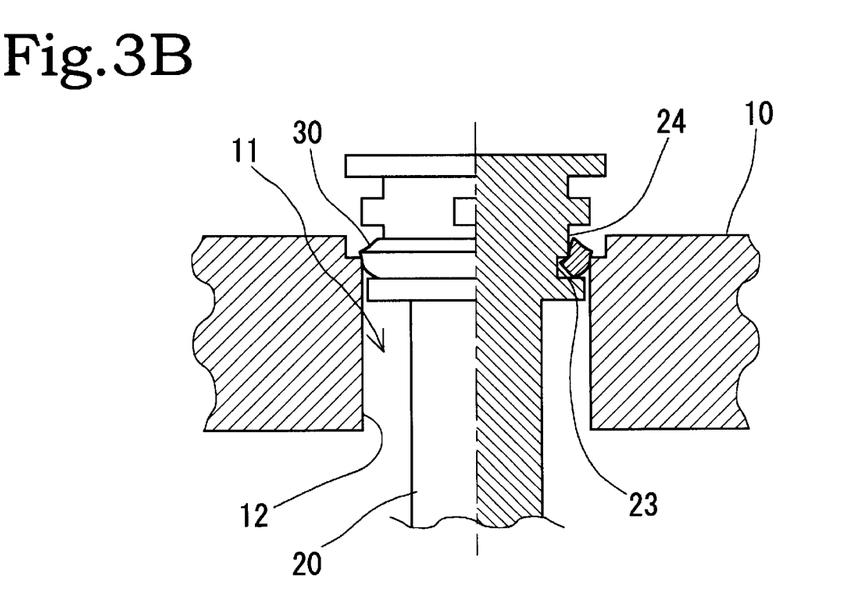
Figure 4A:
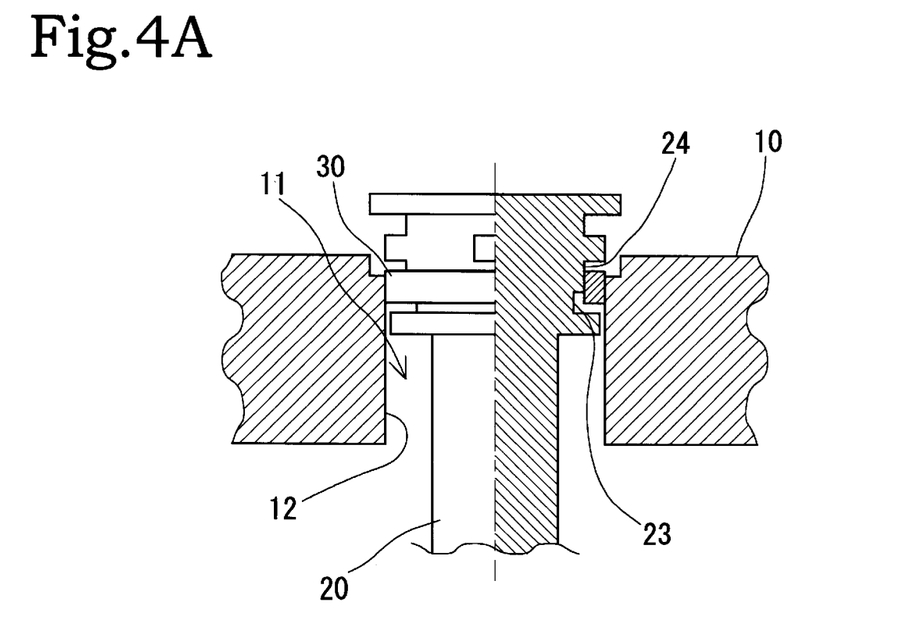
FIGS. 4(A) and 4(B) are descriptive view illustrating a state in which the seal member moves in a seal member-seating portion so as to provide a completed closed condition, after the inserting operation of the plug member of the closure structure of the first embodiment of the present invention.
Figure 4B:
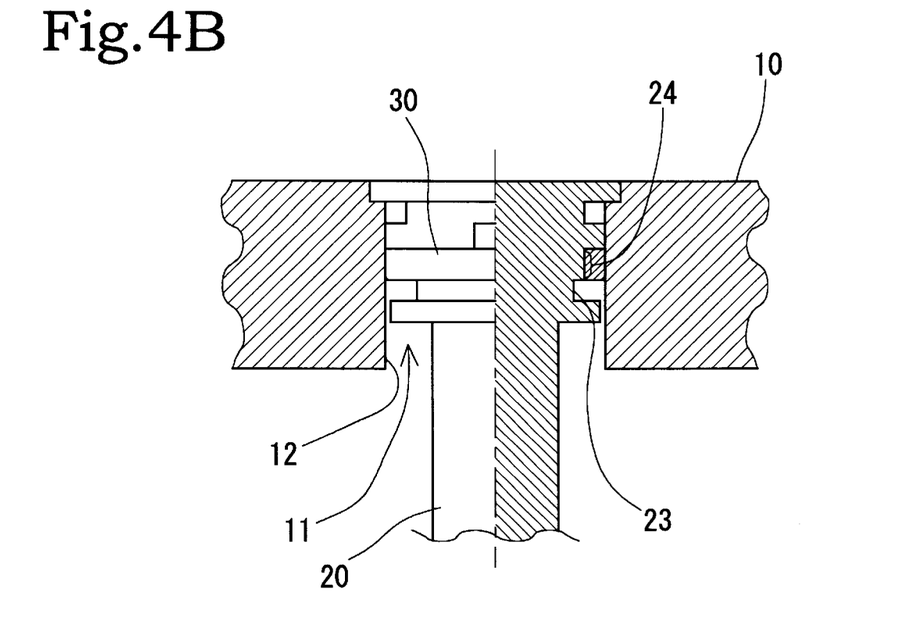

Now, the first embodiment of a closure structure of the present invention will be described in detail below with reference to FIGS. 1 to 4(B). In the embodiment, the present invention is applied to an indicator for a lead battery. FIG. 1 is a partial front view of a plug member constituting a closure structure of the first embodiment of the present invention, FIGS. 2(A) and 2(B) are descriptive views illustrating a state in which an inserting operation of the plug member of the closure structure of the first embodiment of the present invention is started, FIGS. 3(A) and 3(B) are descriptive views illustrating a state in which a seal member is elastically deformed during the inserting operation of the plug member of the closure structure of the first embodiment of the present invention, and FIGS. 4(A) and 4(B) are descriptive view illustrating a state in which the seal member moves in a seal member-seating portion so as to provide a completed closed condition, after the inserting operation of the plug member of the closure structure of the first embodiment of the present invention.

As shown in FIGS. 1 to 4(B), in the closure structure of the embodiment of the present invention, a plug member 20, which is substantially cylindrical and provided in a predetermined position on the outer periphery with a seal member 30 that is formed of elastic material into a ring shape, is inserted into a circular opening hole 11, which is formed on an upper lid 10 of a lead battery serving as the object to be closed, so as to bring the seal member 30 into close contact with the upper lid 10 and the plug member 20, thus closing the opening hole 11.

The plug member 20, which is formed of transparent synthetic resin into a cylindrical shape, is provided at one end thereof with a flange-shaped larger diametrical portion 21, which is larger than the inside diameter of the opening hole 11, and with projections 22 disposed in the vicinity of the larger diametrical portion 21. The diameter of the other portions of the plug member 20 than the larger diametrical portion 21 is smaller than the inside diameter of the above-mentioned opening hole 11. The above-mentioned other portions of the plug member 20 than the larger diametrical portion 21 form an insertion portion to be inserted into the opening hole 11. The plug member 20 has a seal member-receiving groove portion 23 having a predetermined depth, which extends on the outer periphery of the insertion portion in the vicinity of one end thereof. The predetermined portion of the plug member 20, which is placed on the rear side of the seal member-receiving groove portion 23 in the insertion direction of the plug member 20, i.e., in the vicinity of the one end of the plug member 20, serves as a seal member-seating portion 24, which has a cylindrical surface having a predetermined diameter smaller than the inside diameter of the opening hole 11, so that a gap into which the seal member 30 can be deformed to enter, is formed outside the seal member-seating portion 24 when the plug member 20 is inserted into the opening hole 11.

The seal member 30 is a ring-shaped body, which is formed of rubber and has a rectangular cross section. The seal member 30 is fitted on the outer periphery of the plug member 20 so that the axial direction of the former coincides with the axial direction of the latter. The seal member 30 has an inside diameter, which is equal to or smaller than the diameter of the bottom of the seal member-receiving groove portion 23 of the plug member 20, and a predetermined thickness in the axial direction so that the seal member 30 can be received in the seal member-receiving groove portion 23. The seal member 30, which has been received in the seal member-receiving groove portion 23, has an outside diameter, which is larger than the diameter of the opening hole 11, and a thickness in the axial direction, which is equal to or smaller than the width in the diametrical direction.

The seal member 30 has an elastic deformability by which the seal member 30, to which an external force is applied for example during an insertion operation of the plug member, can be deformed so that the thickness the seal member 30 in the axial direction reaches the above-mentioned predetermined length. The seal member 30 has the opposite end faces in the axial direction, which serve as contact surfaces coming into contact with the upper lid 10 and the seal member-seating portion 24 of the plug member 20.

The above-mentioned upper lid 10 forms the upper part of the conventional lead battery. The upper lid 10 has the opening hole 11 formed therein. The upper edge of the inner surface 12 of the opening hole 11 has a recessed portion with a ring shape, into which the larger diametrical portion 21 formed at the one end of the plug member 20 can be fitted so that the upper surface of the plug member 20, which is fitted into the opening hole 11, is flush with the upper surface of the upper lid 10.

Now, description will be given below of an insertion operation of the plug member in the closure structure of the first embodiment of the present invention having the above-described structural features. The seal member 30 is previously fitted in the seal member-receiving groove portion 23 of the plug member 20 to provide a united body. The plug member 20 with the seal member 30 is inserted into the opening hole 11 of the upper lid 10 so that the axial direction of the plug member 20 coincides with the axial direction of the opening hole 11. The outer peripheral edge of the lower end face of the seal member 30, which has the larger diameter than the diameter of the opening hole 11, comes into contact with the peripheral portion of the upper lid 10, which defines the opening hole 11. In this state, there exists resistance force to the insertion force (see FIG. 2(A)).

Application of a further pressing force to the plug member 20 to continue the insertion operation generates reaction force, which is applied from the upper lid 10 to the outer peripheral edge of the lower end face of the seal member 30, against the pressing force applied to the plug member 20. The above-mentioned reaction force elastically deforms the outer peripheral portion of the seal member 30 so that the outer peripheral edge of the lower face of the seal member 30 comes into contact with the inner surface 12 of the upper lid 10, which defines the opening hole 11 and the outer peripheral portion of the seal member 30 is elastically deformed to extend from the initial position in the seal member-receiving groove portion 23 toward the rear end side of the plug member 20 relative to the insertion direction thereof (see FIG. 2(B)).

The inner peripheral edge of the lower end face of the seal member 30 gradually comes off the seal member-receiving groove portion 23, while restraining the inner peripheral edge of the upper end face of the seal member 30 by means of the upper edge of the seal member-receiving groove portion 23, along with the above-mentioned deformation and extension of the outer peripheral portion of the seal member 30 (see FIGS. 3(A) and 3(B)).

During the insertion operation of the plug member 20 into the opening hole 11, the outer peripheral portion of the seal member 30 further extends to the rear side of the plug member 20 relative to the insertion direction to reach the outer surface of the seal member-seating portion 24. The surface, which has served as the upper surface of the seal member 30 in the axial direction thereof, is converted into the inner surface of the seal member 30 so as to come into contact with the seal member-seating portion 24, thus causing the seal member 30 to come off the seal member-receiving groove portion 23 (see FIG. 4(A)). The upper and lower surfaces of the seal member 30 in the axial direction prior to the insertion operation are converted into the inner and outer surfaces of the seal member 30, which come into contact with the seal member-seating portion 24 and the inner surface 12 of the upper lid 10, respectively.

When the insertion portion of the plug member 20 is inserted completely into the opening hole 11, the seal member 30 is almost entirely placed on the outer periphery of the seal member-seating portion 24 so that the entire outer surface of the seal member 30 comes into close contact with the inner surface 12 of the upper lid 10 and the inner surface of the seal member 30 comes into close contact with the seal member-seating portion 24.

The above-mentioned deformation of the seal member 30 to move from the seal member-receiving groove portion 23 to the seal member-seating portion 24 during the insertion operation of the plug member 20 makes it possible to reduce the sliding action of the seal member 30 against the inner surface 12 of the upper lid 10, thus decreasing friction against the insertion of the plug member 20.

In a completely closed state in which the insertion portion of the plug member 20 is fully inserted into the opening hole 11, the outer and inner surfaces of the seal member 30 come into close contact with the upper lid 10 and the seal member-seating portion 24 of the plug member 20, respectively, thus ensuring a sufficiently large contact area to provide an appropriate watertight sealing condition without forming a gap between the upper lid 10 and the plug member 20 (see FIG. 4(B)).

In the embodiment of the closure structure of the present invention, the plug member 20 is provided on its outer periphery with the seal member-receiving grove portion 23 for mounting the seal member 30 and with the seal member-seating portion 24 having the predetermined outside diameter. Inserting the plug member 20, to the seal member-receiving groove portion 23 of which the seal member 30 is fitted, into the opening hole 11 causes the outer peripheral portion of the seal member 30 to be elastically deformed from the initial position in the seal member-receiving groove portion 23 toward the opposite direction to the insertion direction of the plug member 20, under reaction force applied from the upper lid 10 to the outer peripheral edge of the lower end face of the seal member 30, due to the pressing force applied to the plug member 20, while keeping the inner peripheral edge of the end face of the seal member 30 in contact with the seal member-receiving groove portion 23. The opposite end faces of the seal member in the axial direction thereof, which have been kept in a non-deformed state before insertion of the plug member 20 into the opening hole 11, come into close contact with the upper lid 10 and the seal member-seating portion 24, respectively, after insertion of the plug member into it. Accordingly, during the insertion operation of the plug member 20, the seal member 30 is elastically deformed so as to move from the initial position in the seal member-receiving groove portion 23 toward the seal member-seating portion 24, thus preventing the seal member 30 from sliding relative to the upper lid 10 and decreasing frictional resistance during an inserting operation of the plug member 20. In addition, the opposite end faces of the seal member 30, which have the width larger than the thickness thereof in the axial direction, come into close contact with the inner surface of the upper lid 10, which defines the opening hole 11, and the seal member-seating portion 24, respectively, thus ensuring a sufficiently large contact area to provide a sealing condition. As a result, it is possible to insert easily the plug member 20 into the opening hole 11 as well as provide a reliable watertight condition. The insertion operation of the plug member 20 can therefore be carried out effectively and the problem of leakage of liquid can also be avoided.

[Second Embodiment of the Present Invention]

Figure 5:
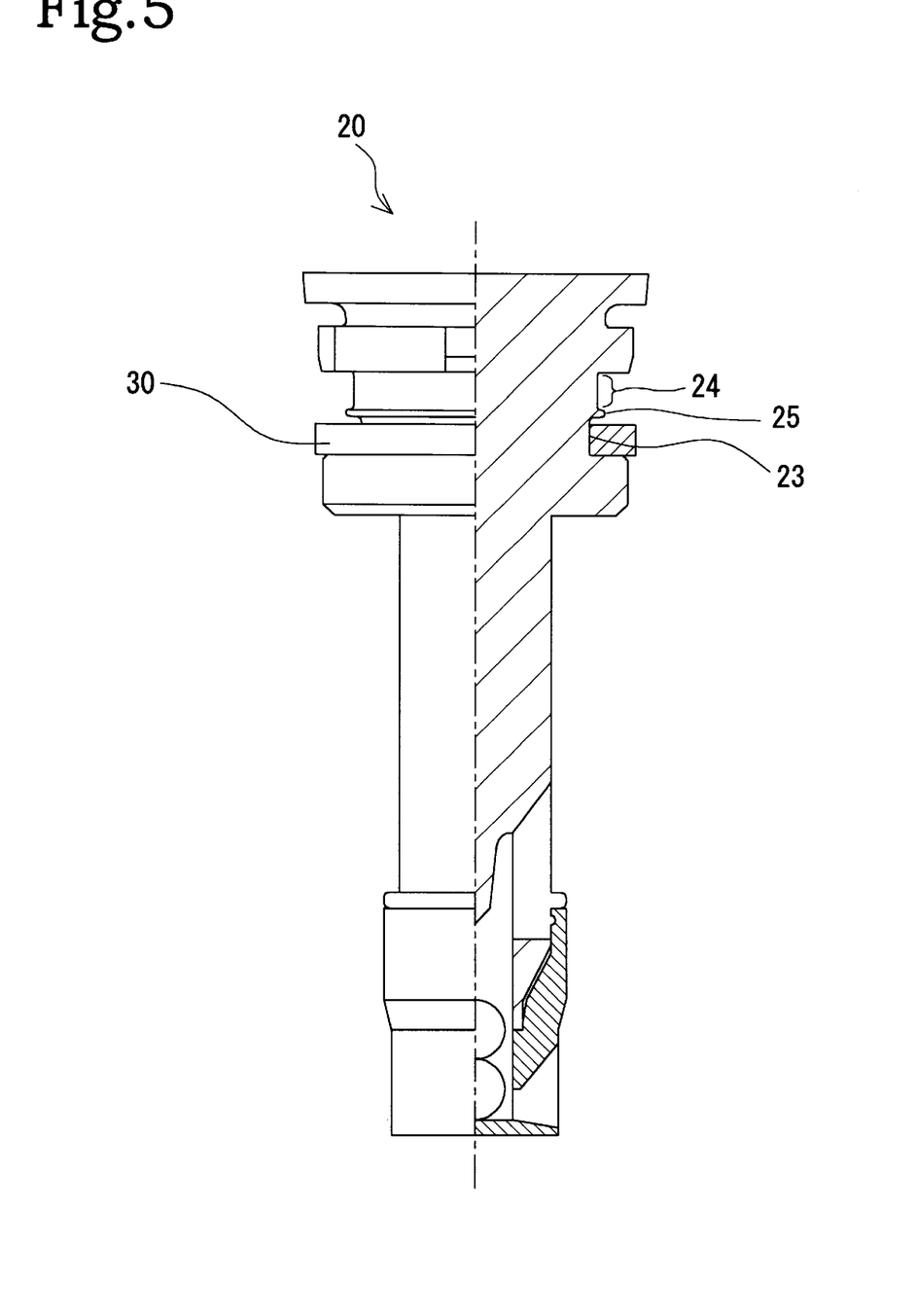
FIG. 5 is a descriptive view of the plug member constituting the closure structure of the second embodiment of the present invention.

Now, the second embodiment of the closure structure of the present invention will be described in detail below with reference to FIGS. 5 and 6. FIG. 5 is a descriptive view of the plug member constituting the closure structure of the second embodiment of the present invention, and FIG. 6 is a descriptive view of the closure structure of the second embodiment of the present invention in the closed condition.

Figure 6:
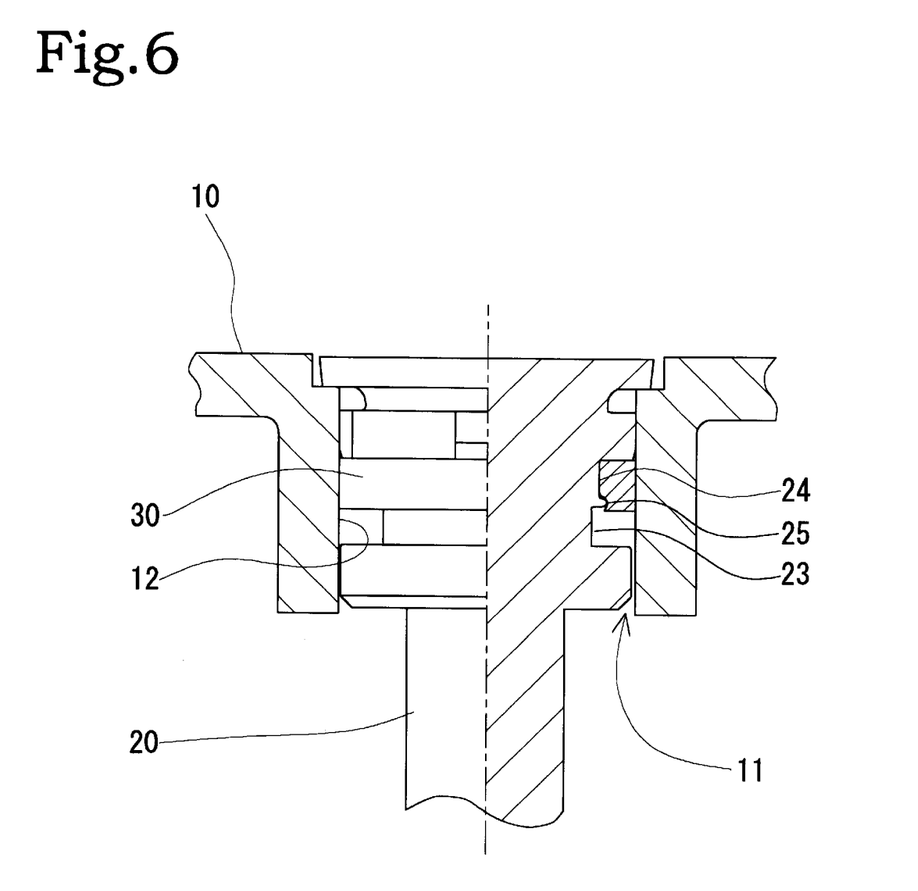
FIG. 6 is a descriptive view of the closure structure of the second embodiment of the present invention in the closed condition.

As shown in FIGS. 5 and 6, in the closure structure of the second embodiment of the present invention, a plug member 20 provided with a seal member 30 is inserted into an opening hole 11, which is formed on an upper lid 10 of a lead battery, so as to bring the seal member 30 into close contact with the upper lid 10 and the plug member 20, thus closing the opening hole 11 in the same manner as the first embodiment of the present invention. The second embodiment differs from the first embodiment in that the plug member is provided on the front side of the seal member-seating portion 24 relative to the insertion direction of the plug member 20 with a flange-shaped seal member-urging projection 25, which has the diameter larger than the seal member-seating portion.

The seal member-urging projection 25 is formed integrally with the lower end of the seal member-seating portion 24 so as to constitute a part of the plug member 20. The seal member-urging projection 25 has a diameter, which is larger than the seal member-seating portion 24. The diameter of the seal member-urging projection 25 is predetermined so as not to prevent the seal member 30 from moving from the seal member-receiving groove portion 23 to the outer surface of the seal member-seating portion 24.

Now, description will be given below of an insertion operation of the plug member in the closure structure of the second embodiment of the present invention having the above-described structural features. When the plug member 20 into the seal member-receiving groove portion 23 of which the seal member 30 has been fitted, is inserted into the opening hole 11 of the upper lid 10, the outer peripheral edge of the lower end face of the seal member 30 comes into contact with the peripheral portion of the upper lid 10, which defines the opening hole 11, and then comes into contact with the inner surface 12 of the upper lid 12. The seal member 30 moves from the seal member-receiving groove portion 23 toward the rear side of the plug member 20 relative to the insertion direction thereof, in accordance with the insertion length of the plug member 20. The inner peripheral edge of the lower face of the seal member 30 is gradually apart from the bottom of the seal member-receiving groove portion 23.

When the plug member 20 is inserted deeper into the opening hole 11, the outer peripheral portion of the seal member 30 reaches the outer surface of the seal member-seating portion 24 so as to come off the seal member-receiving groove portion 23. Consequently, the seal member 30 moves to a region, which is defined by the seal member-seating portion 24 and the seal member-urging projection 25 of the plug member 20 and the inner surface 12 of the upper lid 10, so that the inner surface of the seal member 30 comes into close contact with the seal member-seating portion 24 and the outer periphery of the seal member-urging projection 25, on the one hand, and the outer surface thereof comes into close contact with the inner surface 12 of the upper lid 10.

In the completely closed state of the upper lid 10 with the plug member 20 having the seal member 30, the seal member 30 is forcedly deformed at the portion corresponding to the seal member-urging projection 25, which is provided at the lower end of the seal member-seating portion 24, by a larger amount of deformation in comparison with the other portion. The above-mentioned portion of the seal member 30, which corresponds to the seal member-urging projection 25, comes firmly into close contact with the outer periphery of the seal member-urging projection 25 and the inner surface 12 of the upper lid 10, thus providing an excellent sealing property (see FIG. 5). The seal member-urging projection 25 extending outward strongly pushes the seal member 30 against the inner surface 12 of the upper lid 10, thus ensuring the reliable watertight condition, even when there occurs variations in size of the opening hole 11, and for example, the diameter of the opening hole 11 of the upper lid 10 is slightly larger than the standard value.

In the closure structure of the second embodiment of the present invention, the plug member 20 is provided with the flange-shaped seal member-urging projection 25, which has the diameter larger than the seal member-seating portion 24. The seal member 30 is more strongly pressed between the seal member-urging projection 25 and the inner surface 12 of the upper lid 10 in comparison with the other portion, to be elastically deformed, so that the seal member 30 strongly comes close contact with the outer peripheral surface of the seal member-urging projection 25 and the inner surface 12 of the upper lid 10, under restoring force in accordance with deformation of the seal member 30. It is therefore possible to enhance the sealing property over the entire circumference of the seal member 30, while maintaining the compact structure of the sealed portion and improve the holding property of the watertight condition.

In the closure structure of the first and second embodiments of the present invention, the seal member-receiving groove portion 23 and the seal member-seating portion 24 are disposed so as to be in the vicinity of the one end of the plug member 20. The present invention is not limited only to such embodiments. There may be adopted an optional structure in which the seal member-receiving groove portion 23 and the seal member-seating portion 24 are disposed in a place, which is apart from the one end of the plug member 20, and a seal member-restricting portion having a larger diameter than the seal member-seating portion 24 is disposed on the outer periphery of the plug member 20, which is placed on the rear side relative to the insertion direction of the plug member 20. According to such an optional structure, it is possible to restrict the movement of the seal member 30 relative to the plug member 20 in the opposite direction to the insertion direction of the plug member 20, by means of the seal member-restricting portion, to hold the seal member 30 on the seal member-seating portion 24, thus preventing the seal member 30 from excessively moving from the seal member-receiving groove portion 23, even when an insertion length of the plug member 20 into the opening hole 11 is relatively large. When the plug member 20 is pulled from the opening hole 11, the seal member 30 can smoothly be returned from the seal member-seating portion 24 to the seal member-receiving groove portion 23, thus decreasing sliding resistance of the seal member 30 relative to the inner surface 12 of the upper lid 10 and making it possible to carry out easily a removing operation of the plug member.

In the closure structure of the first and second embodiments of the present invention, the seal member 30, which is to be fitted on the plug member, is a ring-shaped elastic member having the rectangular cross section. The present invention is not limited only to such embodiments. The seal member may have the other cross sectional shape, as long as the seal member can be fitted on the seal member-receiving groove portion 23 and moved to the seal member-seating portion 24 during the insertion operation of the plug member. When the seal member, which has the thickness in the axial direction on the inner peripheral side thereof is larger than the thickness in the axial direction on the outer peripheral side thereof, is fitted on the plug member 20 in such a relationship between the inner and outer peripheral sides, the inserting operation of the plug member 20 causes the seal member at its portion, which is placed on the above-mentioned inner peripheral side and on the front side relative to the insertion direction of the plug member, to be strongly pressed to provide a large amount of elastic deformation. Consequently, the seal member strongly comes into contact with the outer surface of the seal member-seating potion and the inner surface of the upper lid serving as the object to be closed, which defines the opening hole, under the function of restoring force in accordance with deformation of the seal member. It is therefore possible to enhance the sealing property over the entire circumference of the seal member, while maintaining the compact structure of the sealed portion and an easy inserting property. Alternatively, when the seal member having an elastic deformability by which the restoring force in accordance with the amount of deformation on the inner peripheral side of the seal member becomes larger than that on the outer peripheral side thereof, is fitted, in place of the seal member 30 having the uniform elastic deformability, in the seal member-receiving groove portion 23 of the plug member 20 in such a relationship between the inner and outer peripheral sides, it is possible to increase contact pressure of the seal member with the object to be closed and the seal member-seating portion 24, on the front side of the seal member relative to the insertion direction of the plug member, thus enhancing the sealing property.

According to the present invention as described in detail, the plug member is provided on its outer periphery with the seal member-receiving grove portion for mounting the seal member and with the seal member-seating portion having the predetermined outside diameter. Inserting the plug member, to the seal member-receiving groove portion of which the seal member is fitted, into the opening hole causes the outer peripheral portion of the seal member to be elastically deformed from the initial position in the seal member-receiving groove portion toward the opposite direction to the insertion direction of the plug member, under reaction force applied from the object to be closed to the outer peripheral edge of the end face of the seal member in the axial direction thereof, due to insertion force applied to the plug member, while keeping the inner peripheral edge of the end face of the seal member in contact with the seal member-receiving groove portion. The opposite end faces of the seal member in the axial direction thereof, which have been kept in a non-deformed state before insertion of the plug member into the opening hole, come into close contact with the object to be closed and the seal member-seating portion, respectively, after insertion of the plug member into it. Accordingly, when the plug member having the seal member the size of which is so large as to provide a sufficient sealing property is inserted into the opening hole, the seal member is elastically deformed so that the outer peripheral portion of the seal member extends from the initial position in the seal member-receiving groove portion toward the seal member-seating portion, thus preventing the seal member from sliding relative to the object to be closed and decreasing frictional resistance during an inserting operation of the plug member. In addition, the opposite end faces of the seal member come into close contact with the object to be closed and the seal member-seating portion, respectively, thus ensuring a sufficiently large contact area to provide a sealing condition. As a result, it is possible to insert easily the plug member into the opening hole as well as provide a reliable watertight condition.

According to the feature of the second aspect of the present invention, the plug member is provided with the seal member-restricting portion, which has the outside diameter larger than that of the seal member-seating portion, so that the seal member-restricting portion prevents the seal member from moving relative to the plug member in the opposite direction to the insertion direction of the plug member. It is therefore possible to prevent the seal member from moving excessively relative to the plug member in the opposite direction to the insertion direction of the plug member so as to be apart from the seal member-receiving groove portion, thus holding the seal member in the seal member-seating portion in an appropriate manner. Pulling the plug member from the opening hole causes the seal member to move from the seal member-seating portion to the seal member-receiving groove portion, thus decreasing sliding resistance of the seal member relative to the inner surface of the object to be closed and making it possible to carry out easily a removing operation of the plug member.

According to the feature of the third aspect of the present invention, the plug member is provided with the flange-shaped seal member-urging projection, which has the diameter larger than the seal member-seating portion. The seal member is more strongly pressed between the seal member-urging projection and the object to be closed in comparison with the other portion, to be elastically deformed, so that the seal member strongly comes close contact with the outer peripheral surface of the seal member-urging projection and the object to be closed, under restoring force in accordance with deformation of the seal member. It is therefore possible to enhance the sealing property over the entire circumference of the seal member, while maintaining the compact structure of the sealed portion without substantially increasing the contact area of the seal member with the plug member and the object to be closed. In addition, it is possible to ensure the reliable watertight condition, even when there occurs variations in size of the opening hole of the object to be closed.

According to the feature of the fourth aspect of the present invention, there is used the seal member having the cross-section so that the thickness on the inner peripheral side of the seal member in the axial direction thereof is larger than the thickness on the outer peripheral side thereof. The seal member is more strongly pressed at the front side of thereof in the insertion direction of the plug member, in which the above-mentioned inner peripheral side is placed in the closed state, in comparison with the other portion, to be elastically deformed, so that the seal member strongly comes close contact with the outer peripheral surface of the seal member-seating portion and the object to be closed, under restoring force in accordance with deformation of the seal member. It is therefore possible to enhance the sealing property over the entire circumference of the seal member, while maintaining the compact structure of the sealed portion without substantially increasing the contact area of the seal member with the plug member and the object to be closed. In addition, it is possible to ensure the reliable watertight condition, even when there occurs variations in size of the opening hole of the object to be closed.

What is claimed is:

1. A closure structure with a plug member, comprising:
   an object to be closed with a plug member, said object to be closed having an opening hole formed thereon;
   a plug member to be inserted into said opening hole; and
   a seal member disposed on an outer periphery of said plug member, said seal member being formed of a ring-shaped elastic member, said seal member being to be brought into contact with said object to be closed and said plug member so as to close said object to be closed,
   wherein:
      at least an insertion portion of said plug member, which is to be inserted into said opening hole, is smaller than said opening hole, said insertion portion being provided at an outer periphery of a predetermined portion thereof with a seal member-receiving groove, which extends continuously in a circumferential direction of said insertion portion and has a predetermined depth, and said seal member-receiving groove being provided at a predetermined portion thereof, which is placed on a rear side relative to an insertion direction of said insertion portion, with a seal member-seating portion, which has an outer surface with a predetermined diameter, which is smaller than that of said opening hole by a predetermined length and larger than that of a bottom of said seal member-receiving groove; and
      said seal member has a cross-sectional shape, which can be fitted into said seal member-receiving groove of said plug member, said seal member having an outer diameter, which is larger than a diameter of said opening hole in a mounting state into said seal member-receiving groove, said seal member having an elastic deformability by which said seal member, to which an external force is applied, can be deformed so that a thickness thereof in an axial direction reaches at least said predetermined length, and said seal member having opposite end faces in the axial direction, which serve as contact surfaces coming into contact with said object to be closed with the plug and said seal member-seating portion of said plug member.

2. The closure structure as claimed in claim 1, wherein:
   said plug member is provided on a rear side of said seal member-seating portion relative to the insertion direction of said plug member with a seal member-restricting portion, which has an outside diameter larger than that of said seal member-seating portion.

3. The closure structure as claimed in claim 1 or 2, wherein:

said plug member is provided on a front side of said seal member-seating portion relative to the insertion direction of said plug member with a seal member-urging projection having a flange-shape, said seal member-urging projection having a diameter, which is larger than said seal member-seating portion, said diameter of said seal member-urging projection being predetermined so as not to prevent said seal member from moving from seal member-receiving groove portion to an outer surface of said seal member-seating portion.

4. The closure structure as claimed in claim 1 or 2, wherein:

said seal member, which is kept in a non-fitting state to said plug member, has a cross-section so that a thickness on an inner peripheral side of said seal member in the axial direction thereof is larger than a thickness on an outer peripheral side thereof.

* * * * *